United States Patent
Bryant et al.

(10) Patent No.: US 11,446,652 B2
(45) Date of Patent: Sep. 20, 2022

(54) ROTARY PLATFORM FOR CELL LYSING AND PURIFICATION AND METHOD OF USE

(71) Applicant: Siemens Healthcare Diagnostics Inc., Tarrytown, NY (US)

(72) Inventors: Jason Bryant, Eliot, ME (US); Eric Yeaton, Epsom, NH (US); Dan Harris, Deerfield, NH (US); Josiah Hackendorf, Manchester, NH (US); Steven Allen, Nashua, NH (US); Mark Talmer, Pepperell, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/595,802

(22) PCT Filed: May 8, 2020

(86) PCT No.: PCT/US2020/032108
§ 371 (c)(1),
(2) Date: Nov. 24, 2021

(87) PCT Pub. No.: WO2021/002937
PCT Pub. Date: Jan. 7, 2021

(65) Prior Publication Data
US 2022/0143596 A1 May 12, 2022

Related U.S. Application Data

(60) Provisional application No. 62/870,109, filed on Jul. 3, 2019.

(51) Int. Cl.
*B01L 3/00* (2006.01)
*C12N 1/06* (2006.01)

(52) U.S. Cl.
CPC .............. *B01L 3/502* (2013.01); *C12N 1/066* (2013.01); *B01L 2200/0631* (2013.01); *B01L 2200/0647* (2013.01); *B01L 2300/0803* (2013.01)

(58) Field of Classification Search
CPC ............. B01L 3/502; B01L 2200/0631; B01L 2200/0647; B01L 2300/0803; C12N 1/066
(Continued)

(56) References Cited

U.S. PATENT DOCUMENTS

| 4,456,581 A | 6/1984 | Edelmann et al. |
| 4,933,147 A | 6/1990 | Hollar et al. |

(Continued)

FOREIGN PATENT DOCUMENTS

| WO | WO-2015047190 A1 * | 4/2015 | ........ B01L 3/502738 |
| WO | 2015075563 | 5/2015 | |

OTHER PUBLICATIONS

International Search Report for PCT/US2020/032108 dated Jul. 22, 2020.

*Primary Examiner* — Benjamin R Whatley
*Assistant Examiner* — Jacqueline Brazin (57) ABSTRACT

Magnetic beads having cell components of interest are translated between a sequence of processing wells in a tray without need for pipetting. The circular tray contains one or more sequences of wells each interconnected by a respective channel. The tray is rotated about a central axis and a magnet, an agitator, and a heater provided external to the tray enable magnetic bead translation, mixing, and incubation, respectively. The magnet proximate a well forms a cluster of beads. Manipulation of the tray in rotation and elevation results in translation of the cluster from one well, through a channel, and into an adjacent well. The well containing a cluster may be rotationally positioned in front (Continued)

of the agitator, the agitator extended into contact with the well, followed by mechanical agitation. The heater, disposed beneath the tray, may accept a well lowered thereto for selective heating.

17 Claims, 8 Drawing Sheets

(58) Field of Classification Search
USPC .......................................................... 435/259
See application file for complete search history.

(56) References Cited

U.S. PATENT DOCUMENTS

| | | | |
|---|---|---|---|
| 5,242,803 A * | 9/1993 | Burtis | B01L 3/502753 |
| | | | 435/7.92 |
| 5,283,178 A * | 2/1994 | Kessler | G01N 33/5304 |
| | | | 436/805 |
| 5,643,168 A | 7/1997 | Piramoon et al. | |
| 6,857,997 B2 | 2/2005 | Yamada et al. | |
| 8,703,070 B1 | 4/2014 | Parng et al. | |
| 10,086,383 B2 | 10/2018 | Piramoon | |
| 2004/0018116 A1* | 1/2004 | Desmond | C12Q 1/686 |
| | | | 422/502 |
| 2018/0003704 A1* | 1/2018 | Horii | G01N 35/10 |

* cited by examiner

ROTARY PLATFORM FOR CELL LYSING AND PURIFICATION AND METHOD OF USE

FIELD OF THE DISCLOSURE

The disclosure herein relates generally to the field of cell lysing, purification, and elution. More particularly, the present disclosure relates to a rotary, multi-well tray having particular utility in the field of cell lysis, purification, and elution in molecular diagnostics.

BACKGROUND

In typical cell lysis and purification systems, magnetic beads used to capture desired sample components such as DNA and RNA are kept in one well or some other processing space while unwanted sample fluid is removed from the well and wash and other buffers are added to the well by a pipetting system. During the fluid removal process, the magnetic beads are captured and retained by an external magnet. When another fluid is reintroduced into the well, the beads are typically released from the influence of the magnet to enable turbulent mixing.

An alternative approach as practiced in the prior art is to move the magnetic beads, and associated target components, from well to well to carry out a sequence of washing steps prior to elution. This may be carried out, for example, through use of a magnet disposed within a disposable cover and inserting the combination directly into the well containing the magnetic beads. Once the beads have been transferred to a new well, the combined magnet and disposable cover may be retracted, or the magnet may be retracted from the disposable cover. Agitation is preferably employed to enhance washing and elution. The use of heat for sample processing may further complicate such prior art approaches.

Innovations directed at streamlining automated cell lysis and purification, minimizing the number of consumables, and simplifying the application of external factors such as agitation and heat would be highly desirable.

SUMMARY

In order to overcome the complexity of the prior art systems and processes for cell lysis, purification, and elution, the present disclosure provides for the transport of magnetic beads having associated therewith nucleic acids or other cell components of interest along a unique pathway within a substantially circular consumable tray. The tray is rotated about a central axis and a magnet, an agitator such as ultrasonic actuator, and a heater are provided external to the consumable tray.

The circular tray may contain one or more sequences of wells to support one or more discrete and unique sample preparation sequences. This allows for ultrasonic assisted lysing, washing, and magnetic bead manipulation via external magnet attraction rather than through the use of one or more pipette heads and associated disposable pipetting tips. Multiple trays may be integrated into a single system, thereby allowing for the asynchronous operation of each tray. This provides an improvement in flexibility, parallelism, and equipment redundancy in sample processing.

Each tray provides at least one sequence of interconnected wells. In an embodiment illustrated below, two sequences of wells per tray are provided on opposite tray sides. Each well within a sequence is connected to at least one other well by a channel therebetween. An external magnet may be disposed in proximity to an exterior surface of the fluid wells and the channel. This magnet is held stationary, next to the tray, where magnetic beads are gathered into a cluster adjacent the well or channel exterior wall. Manipulation of the tray in rotation and elevation results in the magnetic bead cluster transitioning between the interior of one well, up to a channel, and into an adjacent well. Changes in rotational and elevational position are implemented by an actuator on which the tray is suspended. Once the magnetic particles enter the next fluidic well, the magnet is retracted and the particles are able to be resuspended into the fluid through mixing.

Mixing can be performed in a variety of ways. A direct approach is to rotate the tray back and forth about the central axis of symmetry through selective actuation of the actuator upon which the tray is suspended. This agitation in combination with well geometry enables fluids and magnetic beads inside a well to move about and mix up the liquids and solid particles.

Another method of mixing includes the use of an external agitating apparatus. Positioned external to the tray in a manner similar to the external magnet, the well containing magnetic beads may be rotationally positioned in front of the agitator through rotational actuation of the actuator. The agitator may then be extended forward and into contact with the target well. Mechanical agitation may then be implemented. The agitation may be ultrasonic, for example. Upon completion of agitation, the agitator may be retracted to avoid mechanical interference with the subsequent rotational or elevational movement of the tray.

Other methods of agitation may include mixing bars or stirring rods disposed within selected wells, vibration of the entire tray, orbital mixing, and sonication.

In addition, a system implementing the presently disclosed lysis and sample preparation disposable tray and a method of use may further include a heater normally disposed beneath the tray, except when the tray is lowered by the actuator to a height where one well, aligned with the heater, is lowered into the heater for a desired temporal period. Such heating may be an adjunct to the cell lysis process, elution, or any other step.

Magnetic beads are contained within the disposable tray the entire time, thus eliminating any dripping or contamination such as may occur with bead transfer or fluid pipetting. Obviating the use of external resources for inserting a magnet in a disposable sleeve or for pipetting thus makes the presently disclosed process more time efficient. The need for disposable sample tips is obviated. Multiple well sequences on one tray enable the simultaneous processing of multiple samples. Bulk loading of liquids such as lysis, wash, and elution buffers and of magnetic beads prior to processing reduces test duration.

BRIEF DESCRIPTION OF THE DRAWINGS

Illustrative embodiments of the disclosed technology are described in detail below with reference to the attached drawing figures, which are incorporated by reference herein and wherein.

DETAILED DESCRIPTION

Disclosed herein is a rotary platform for cell lysing, sample purification, and elution. Use of the platform enables simplified movement of magnetic particles or beads and associated sample fragments such as nucleic acids through a multi-stage cell lysis and purification protocol without the requirement for external pipetting systems and associated pipetting tips.

A rotary tray having at least one sequence of processing wells distributed along a periphery thereof is mounted for selective rotation and elevation relative to an extendable and retractable magnet. The magnet enables selective attraction of magnetic beads into a cluster within a well. Coordinated movement of the tray in rotation and elevation enables the magnetic bead cluster to be moved from well to well without the use of a pipetting system or associated disposable tips and while the magnet remains stationary. The system may also include an extendable and retractable agitator for selective agitation of the contents of a well, such as for purposes of washing. In addition, a heater may be located beneath the tray and offset from an axis of symmetry of the tray such that a well may be aligned above the heater, the tray lowered, and the aligned well received within the heater for a desired period of heating, such as for lysing or elution.

Figure 1:
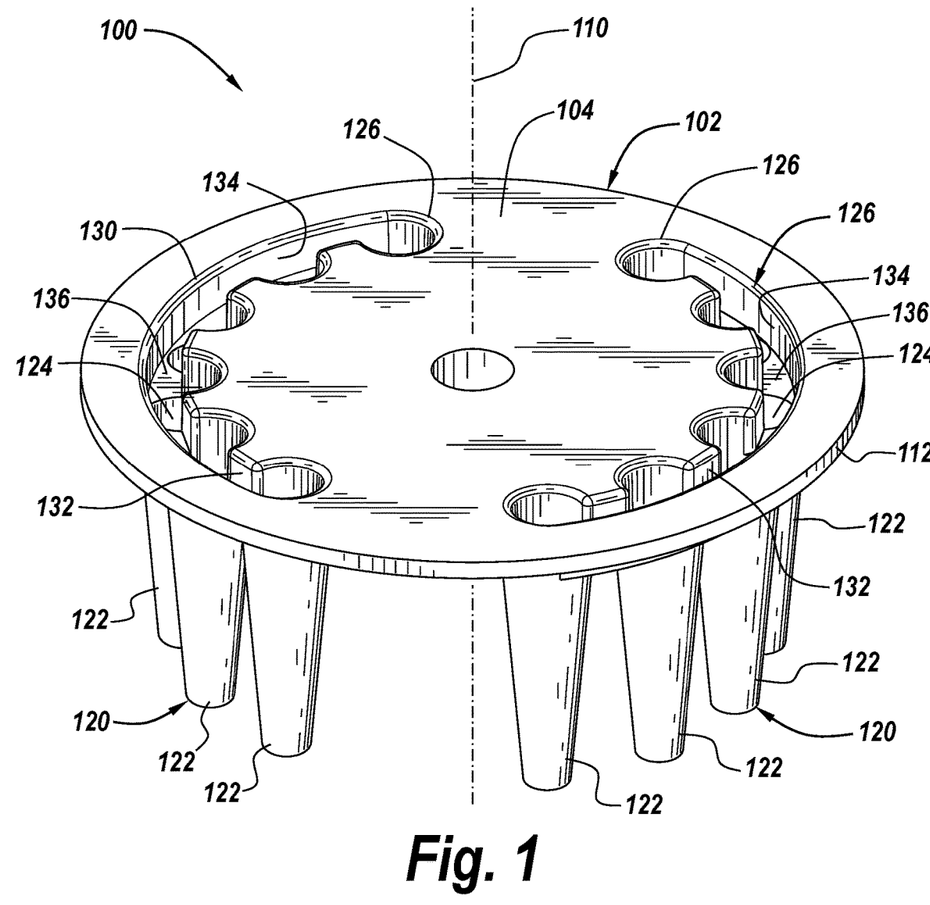
FIG. 1 is a perspective view of a rotary platform having plural well sequences each interconnected by a respective channel according to the present disclosure.
Figure 2:
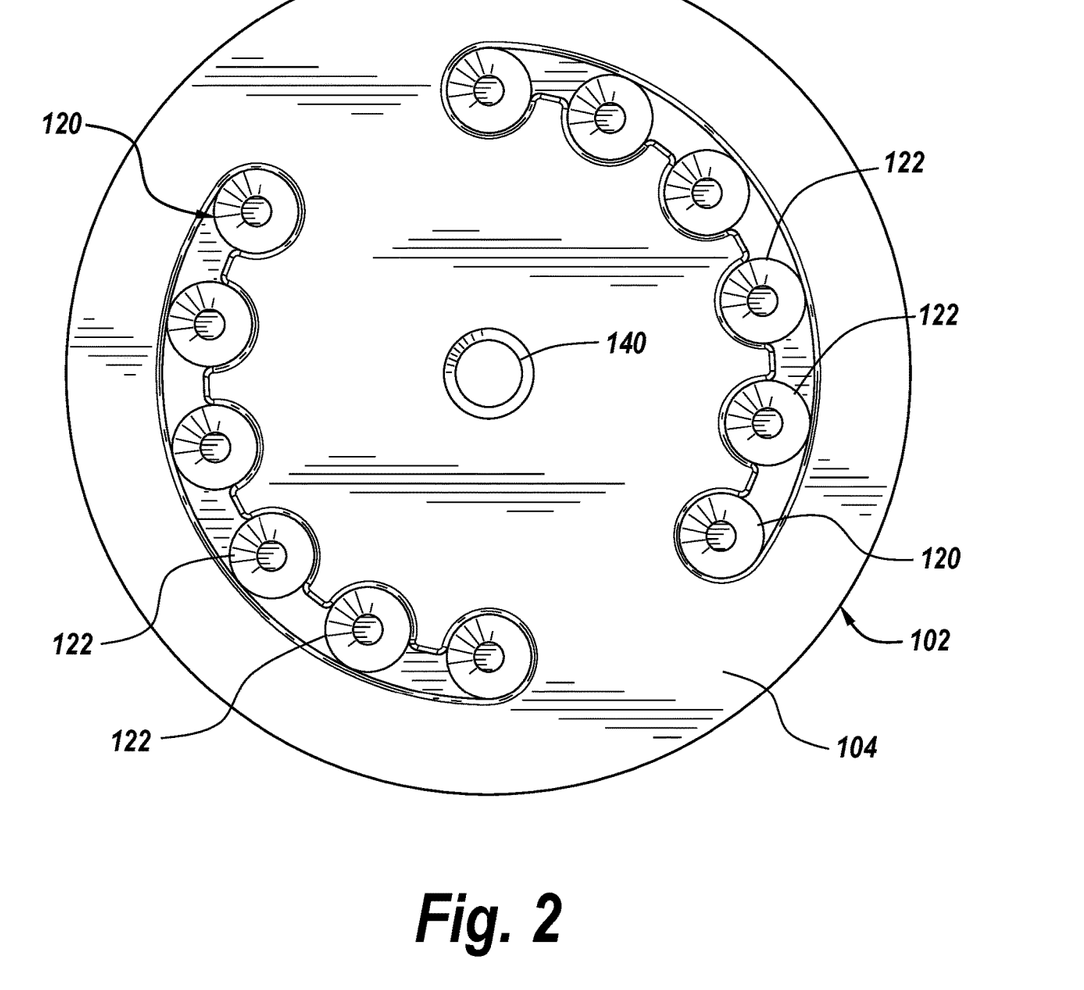
FIG. 2 is a top view of the rotary platform of FIG. 1.
Figure 3:
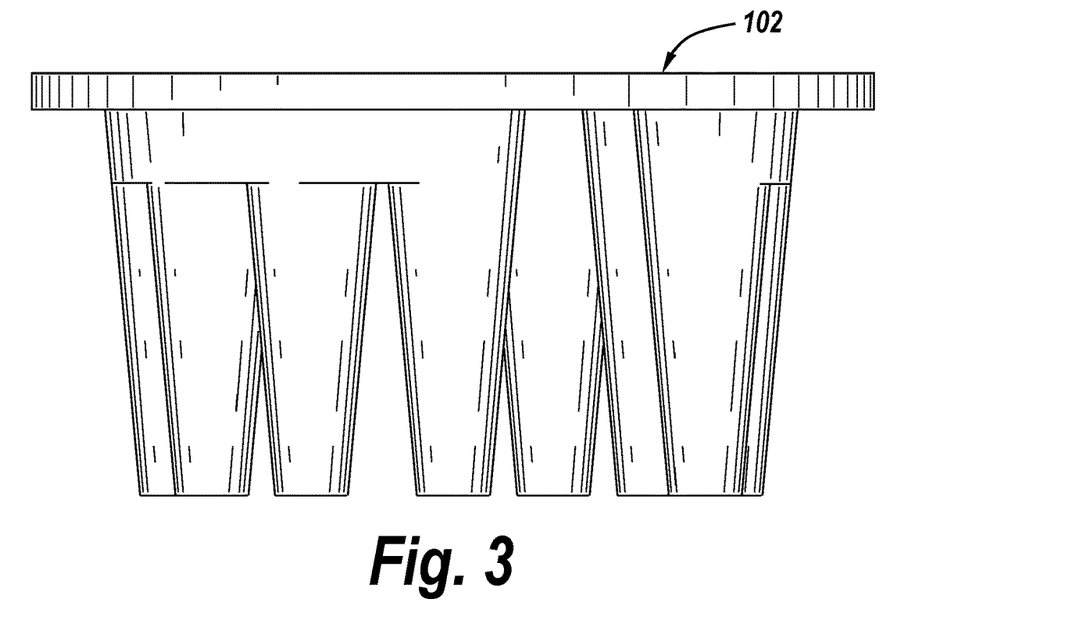
FIG. 3 is front elevation view of the rotary platform of FIG. 1.
Figure 4:
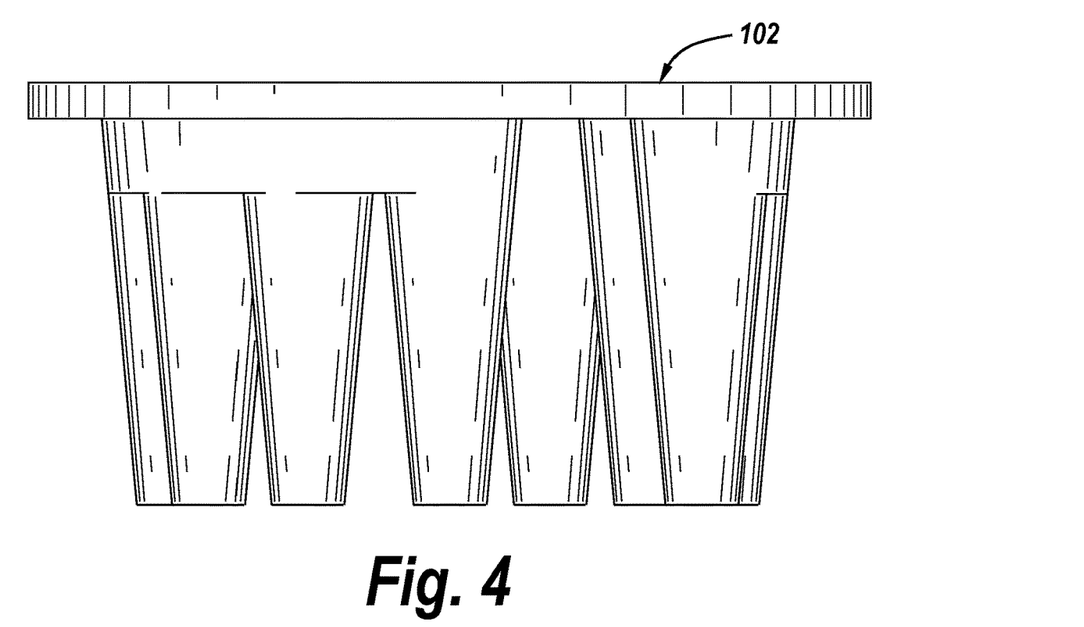
FIG. 4 is a rear elevation view of the rotary platform of FIG. 1.
Figure 5:
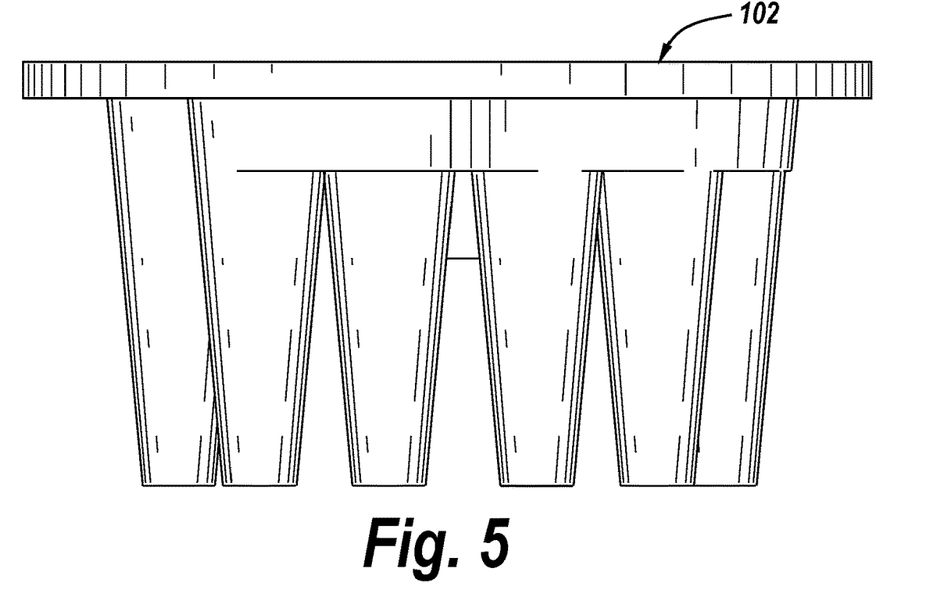
FIG. 5 is a right side elevation view of the rotary platform of FIG. 1.
Figure 6:
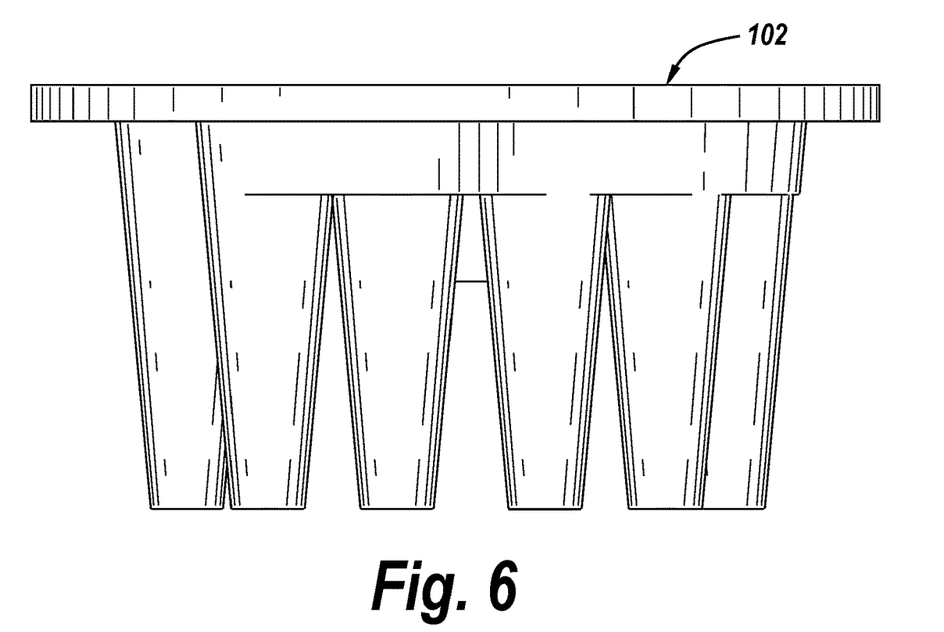
FIG. 6 is a left side elevation view of the rotary platform of FIG. 1.
Figure 7:
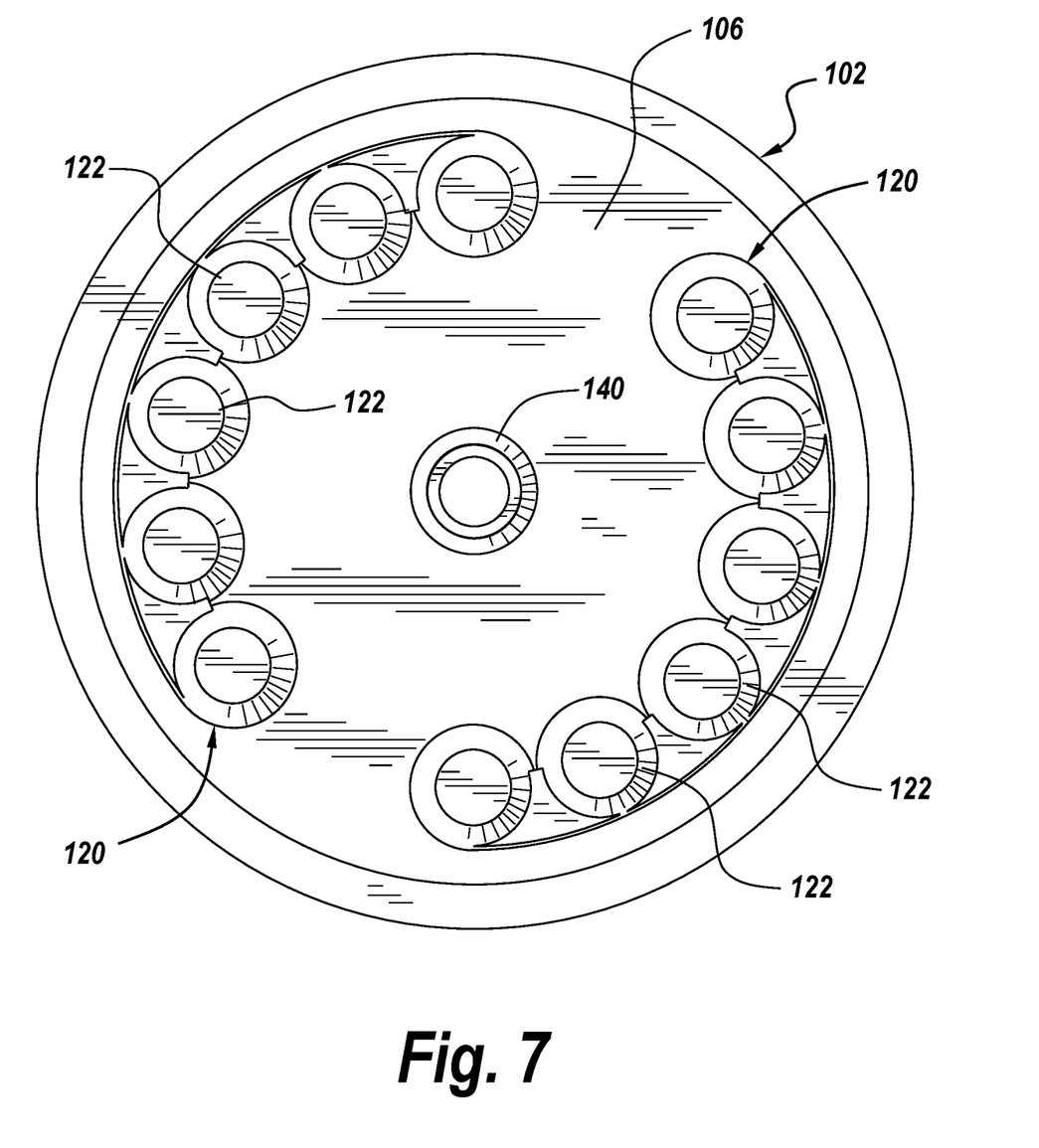
FIG. 7 is a bottom view of the rotary platform of FIG. 1.
Figure 8:
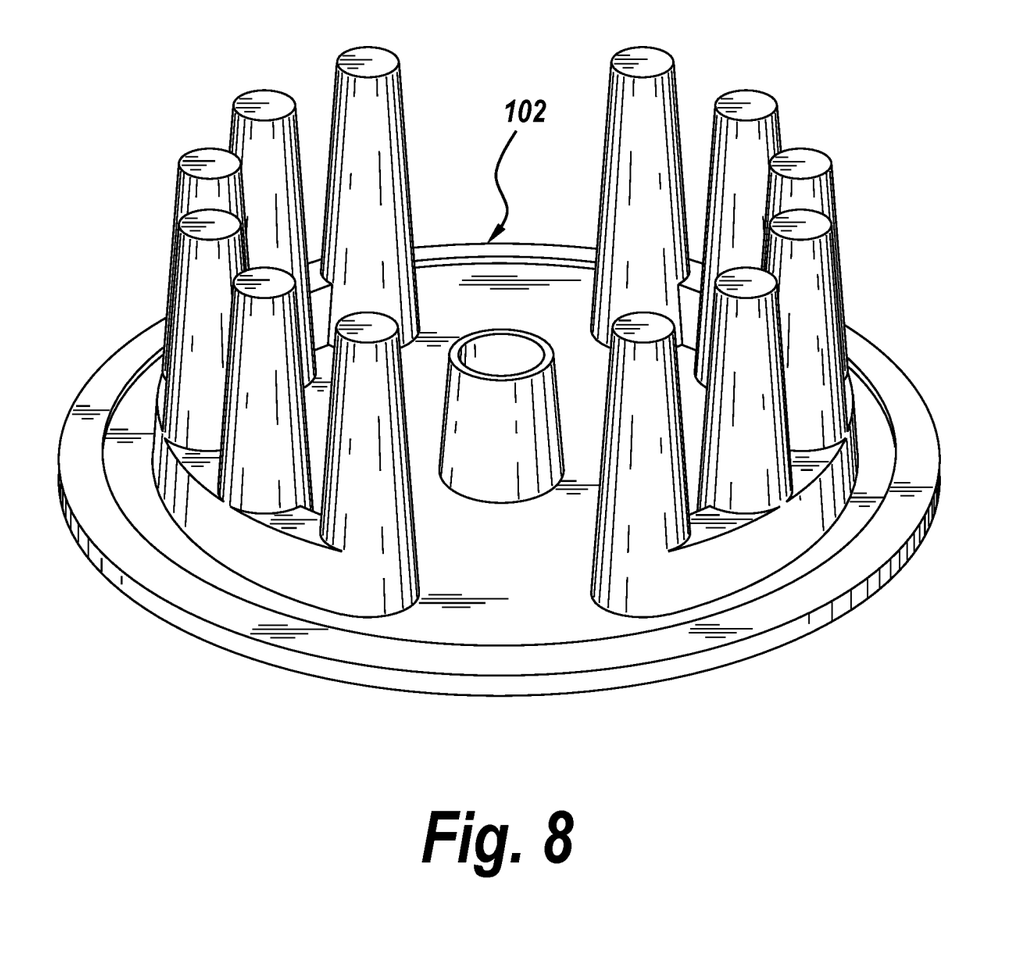
FIG. 8 is a bottom perspective view of the rotary platform of FIG. 1.

With regard to FIG. 1, a rotary platform 100 for cell lysing, purification, and elution is shown. The platform comprises a substantially circular tray 102 having an upper surface 104 and an opposite lower surface 106 (FIG. 7), the upper and lower surfaces defining a thickness therebetween. A vertical axis of symmetry 110 passes through the center of the tray, orthogonal to the upper and lower surfaces thereof. The tray outer extent is defined by an outer radial edge 112. The tray further includes a rotor mating interface 140 (FIGS. 2 and 7) coaxial with the axis of symmetry for mechanically mating to an actuator 302 via a rotor 304 configured to selectively rotate and adjust the elevation of the tray, as will be discussed subsequently.

Disposed in conjunction with the tray 102 is at least one sequence 120 each comprising plural wells 122. In the figures, there are two such sequences per tray, symmetrically distributed about the axis of symmetry 110. As can be seen in FIG. 1, each well has an outer surface that extends from the lower surface 106 of the tray about a periphery of the tray in an arc equidistant from the axis of symmetry. The outer surface as illustrated is frustoconical and extends substantially orthogonal to the tray lower surface, narrowing as the well extends distal from the tray.

Each well 122 has an interior volume 124 and an associated opening 126 in the tray upper surface 104. The opening of each well extends into the respective interior volume. Each opening is substantially circular and coplanar with the tray upper surface 104, except where it is intersected by a channel 130 of the respective well sequence 120.

The channel 130 is formed in the tray upper surface 104. The channel connects each adjacent pair of wells 122 within a sequence 120 of wells. Thus, as there are two sequences of wells in the presently illustrated embodiment, there are two channels, one for each sequence.

The depth of each channel 130 is less than the thickness of the tray 102 between the upper 104 and lower 106 surfaces. Intermediate each pair of wells, the channel has inner walls 132 and an outer wall 134. The inner and outer walls intersect the openings 126 of the adjacent wells.

All points on the inner walls 132 have the same radial distance from the tray 102 axis of symmetry 110. This radial distance is the same as the radial distance between the axis of symmetry and the center point of each circular opening 126 associated with each well 122. Similarly, all points on the outer wall 134 have the same radial distance from the axis of symmetry. The outer wall radial distance is greater than that of the inner walls. The radial distance from the axis of symmetry for points on the outer wall is the same as the maximum radial distance from the axis of symmetry to each well opening 126. Each channel 130 also includes a floor surface 136 that is substantially parallel to and intermediate the upper 104 and lower 106 surfaces of the tray 102.

Figure 9:
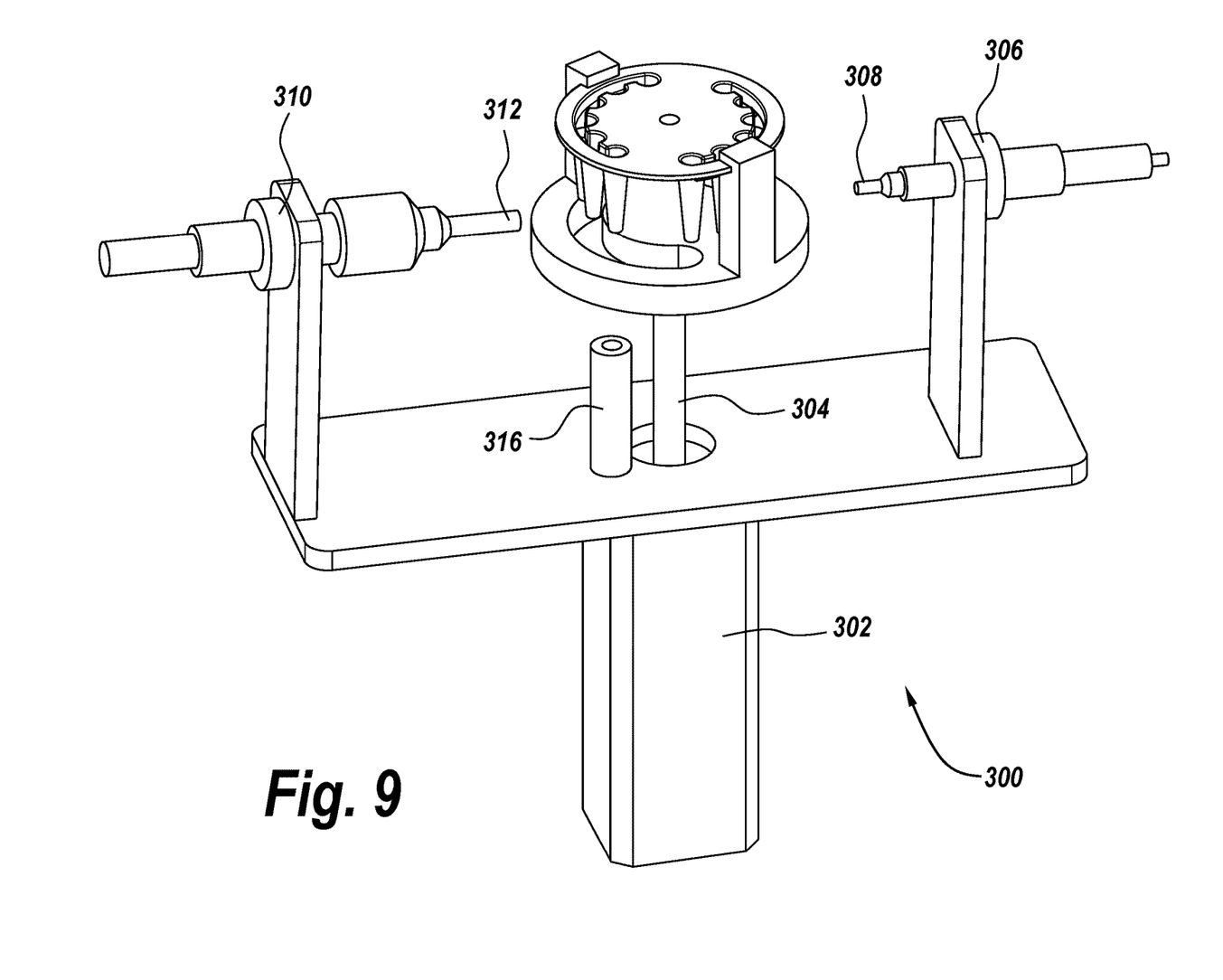
FIG. 9 is a system for cell lysing and purification incorporating the rotary platform of FIG. 1 according to the present disclosure.

The rotary platform 100 as described in the foregoing may be used in a system 300 for cell lysing, purification, and elution. As seen in FIG. 9, in addition to the previously described platform, the system includes an actuator 302 having a rotor 304. The actuator enables the selective rotation and adjustment in elevation of the platform. Specifically, the rotor 304 is configured to mate with a tray 102 mating interface 140 (FIGS. 2 and 7) that is coaxial with the tray axis of symmetry 110. The actuator, under control of a controller as known to one skilled in the art, is capable of selectively rotating the tray and adjusting its height.

The system 300 also includes a magnetic member 306 adapted to selectively extend and retract a magnet 308 with respect to a first position adjacent the tray 102 in a horizontal plane. In addition, an agitating member 310 is adapted to selectively extend and retract an agitating tip (also referred to herein as an agitator) 312 with respect to a second position adjacent the tray 102 in a horizontal plane. The agitating member is also capable of imparting agitating motion in the agitating tip. The magnetic member and the agitating member may also be under control of the same or distinct programmable controllers. In the illustrated embodiment, the first and second positions are separated by 180 degrees about the tray.

The system may further comprise a heater 316 disposed beneath the tray 102 and, in particular, offset from the tray 102 axis of symmetry 110 the same distance as the wells 122.

Thus, through coordinated movement of the rotary platform 100, the actuator 302, magnetic member 306, agitating member 310, and heater 316, a method of lysing, purifying, and eluting a sample may be carried out. This method is described with respect to FIG. 10.

Figure 10:
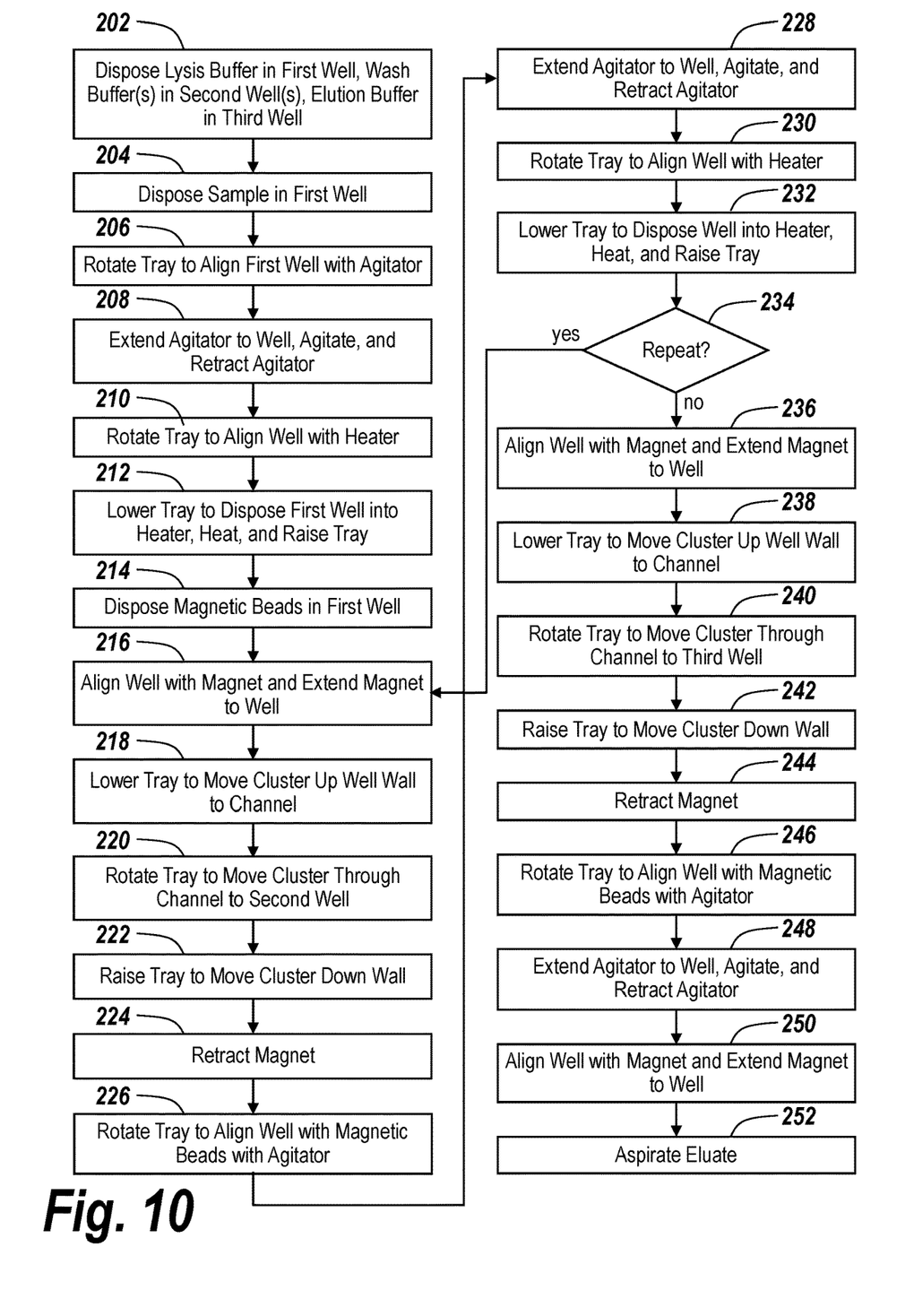
FIG. 10 is a flowchart of a presently disclosed process for cell lysis, purification, and elution employing the system of FIG. 9.

Lysis buffer is disposed 202 in a first well 122 of a sequence of wells 120, wash buffer is disposed in one or more second wells, and elution buffer is disposed in a third well. Ideally, a bulk liquid loader (not illustrated) may be used for this purpose in order to expedite the testing method.

A quantity of fluid sample may then be disposed 204 into the first well 122, previously loaded with lysis buffer, through the use of a pipetting system (not illustrated). The actuator 302 is then activated to align 206 the first well with the agitating member. The agitating tip 312 is extended 208 laterally towards the first well, and the agitating tip agitates the first well exterior surface. Such agitation may, for example, by ultrasonic. After agitation, the agitating tip is retracted.

Next, the tray 102 is again rotated 210 by the actuator 302 via the rotor 304 to align the first well 122 with the heater 316. The tray is lowered 212 through adjustment in tray height via the actuator, by which the first well is lowered into the heater. A desired temperature or temperature profile is applied to the well for a desired temporal period. The tray is the elevated by the actuator.

Magnetic beads are then disposed 214 within the first well 122, and the tray 102 is rotated 216 by the actuator 304 to align the target well with the magnetic member 306. The magnet 308 is extended by the magnetic member to a position proximate the target well, allowing magnetic beads to cluster on the well inner wall near the magnet.

With the magnet remaining extended, the actuator 302 lowers 218 the tray. Since the cluster of magnetic beads is held in vertical position by the magnet, the cluster is effectively dragged into the channel 130 as the tray descends. Next, the actuator rotates 220 the tray 102 thereby moving the relative location of the cluster through the channel into the upper extent of the second well 122. The actuator then raises 222 the tray, thereby positioning the cluster into the lower extent of the second well. The magnetic member 306 then retracts 224 the magnet 308, releasing the cluster of magnetic beads from the well side wall.

To enhance the dispersion of the magnetic beads, with sample components of interest attached thereto, the tray is again rotated 226 about the axis of symmetry 110 by the actuator 302 to align the target well 122 with the agitating member 310. The agitating tip 312 is extended 228 and the well is agitated, following which the agitating tip is retracted.

Optionally, the tray 102 is once again rotated 230 to the heater 316, the tray is lowered 232, disposing the target well into the heater, the well is heated as desired, and the tray is elevated.

The cycle of clustering the magnetic beads, moving them from one well into the channel and into the next well, retracting the magnet, agitating the well contents, and optionally heating the well contents may be repeated 234 for each subsequent second well having wash buffer therein.

Once the last wash iteration has been completed, the actuator 302 aligns 236 the target second well having magnetic beads with sample components associated therewith with the magnetic member 306, and the magnet 308 is extended into proximity with the target well. The tray 102 is lowered 238 by the actuator 302, thereby moving the cluster up the well wall to the channel 130. The tray is again rotated 240 to move the cluster through the channel to the third well, which is the elution well. The tray is raised 242 to locate the cluster at a lower extent of the respective well, and the magnet is retracted 244. The magnetic beads are again dispersed by rotating 246 the tray to align the target well with the agitating member 310, which extends 248 the agitating tip 312 to the well, agitates the contents thereof, then retracts the agitating tip.

The tray is again rotated 250 to align the target well with the magnetic member 306 and the magnet 308 is extended to attract the magnetic beads from which the components of interest have been released by the elution buffer and agitation. The eluate is then aspirated 252. While not illustrated, the method may further include rotating the target well to the heater for incubation after agitation and prior to attracting the magnetic beads and removing the eluate.

The tray 102 may then be removed from the mating interface 140 and transferred to a waste receptacle, following which a new tray may be provided.

The foregoing description has been directed to particular embodiments. However, other variations and modifications may be made to the described embodiments, with the attainment of some or all of their advantages. It will be further appreciated by those of ordinary skill in the art that modifications to the above-described systems and methods may be made without departing from the concepts disclosed herein. Accordingly, the invention should not be viewed as limited by the disclosed embodiments. Furthermore, various features of the described embodiments may be used without the corresponding use of other features. Thus, this description should be read as merely illustrative of various principles, and not in limitation of the invention.

Many changes in the details, materials, and arrangement of parts and steps, herein described and illustrated, can be made by those skilled in the art in light of teachings contained hereinabove. It will be understood that certain features and sub-combinations are of utility and may be employed without reference to other features and sub combinations and are contemplated within the scope of the claims. Accordingly, it will be understood that the following claims are not to be limited to the embodiments disclosed herein and can include practices other than those specifically described, and are to be interpreted as broadly as allowed under the law. Additionally, not all steps listed in the various figures need be carried out in the specific order described.

We claim:

1. A rotary platform comprising:
    a substantially circular tray having an upper surface, a lower surface, a thickness between the upper surface and the lower surface, an axis of symmetry orthogonal to the upper and lower surfaces, and an outer radial edge;
    a sequence of plural wells, each well having an outer surface extending from the lower surface of the tray about a periphery of the tray and having an interior volume and an opening in the tray upper surface, the opening extending into the respective well interior volume, the wells of the sequence of plural wells being disposed in an arc equidistant from the axis of symmetry; and
    a channel formed in the tray upper surface, the channel intersecting the opening of each of the plural wells in the respective sequence, the channel extending between the openings of the adjacent wells of the plural wells, and the channel describing an arc equidistant from the axis of symmetry.

2. The rotary platform of claim 1, wherein each well outer surface is frustoconical.

3. The rotary platform of claim 1, wherein each well extends substantially orthogonally from the lower surface of the tray.

4. The rotary platform of 2, wherein the outer surface of each well outer surface narrows in a direction distal from the tray.

5. The rotary platform of claim 1, wherein the channel has inner walls and an outer wall, all points on each of the inner and outer walls having a respective identical radial distance from the axis of symmetry, and each inner wall extends between adjacent wells in the sequence.

6. The rotary platform of claim 5, wherein the channel has a floor that is parallel to and intermediate the tray upper and lower surfaces.

7. The rotary platform of claim 5, wherein each well opening is substantially circular and coplanar with the tray upper surface, and
wherein the channel outer wall has an outer wall radial distance, relative to the axis of symmetry, that is substantially equal to a maximum radial distance, relative to the axis of symmetry, of the opening of each of the adjacent wells of the plural wells in the sequence.

8. The rotary platform of claim 7, wherein each substantially circular opening has a respective center point located at a center point radial distance, relative to the axis of symmetry, and
wherein each channel inner wall has an inner wall radial distance, relative to the axis of symmetry, that is substantially equal to the center point radial distance of each of the adjacent wells of the plural wells in the sequence.

9. The rotary platform of claim 1, further comprising a rotor mating interface coaxial with the axis of symmetry.

10. The rotary platform of claim 1, wherein the sequence of plural wells is a first sequence of plural wells and the channel is a first channel, and wherein the rotary platform further comprises a second sequence of plural wells, identical to the first sequence of wells, and a second channel, identical to the first channel.

11. The rotary platform of claim 10, wherein the first and second sequences of plural wells are symmetrically distributed about the periphery of the tray.

12. A system comprising:
a rotary platform, comprising
a substantially circular tray having an upper surface, a lower surface, a thickness between the upper surface and the lower surface, an axis of symmetry orthogonal to the upper and lower surfaces, and an outer radial edge,
first and second sequences of plural wells, each well having an outer surface extending from the lower surface of the tray about a periphery of the tray and having an interior volume and an opening in the tray upper surface, the opening extending into the respective well interior volume, the wells of each sequence of plural wells being disposed in an arc equidistant from the axis of symmetry,
a channel formed in the tray upper surface, the channel intersecting the opening of each of the plural wells in the respective sequence, the channel extending between the openings of the adjacent wells of the plural wells, and the channel describing an arc equidistant from the axis of symmetry, and
a rotor mating interface coaxial with the axis of symmetry,
wherein the channel has inner walls and an outer wall intersecting the openings of the adjacent ones of the plural wells in the respective sequence, all points on each of the inner and outer walls having a respective identical radial distance from the axis of symmetry, and each inner wall extends between adjacent wells in the sequence, and
wherein the channel has a floor that is parallel to and intermediate the tray upper and lower surfaces;
a vertically aligned rotor in mechanical communication with the rotor mating interface for imparting selective rotation and elevational movement of the rotary platform; and
a magnetic member configured to selectively horizontally extend and retract a magnet with respect to a first position adjacent to the tray, wherein the magnet is disposed on the magnet member.

13. The system of claim 12, further comprising an agitating member configured to selectively horizontally extend and retract an agitator with respect to a second position adjacent to the tray, wherein the agitator is disposed on the agitating member.

14. The system of claim 13, wherein the first and second positions are separated by 180 degrees about the tray.

15. The system of claim 12, wherein each well opening is substantially circular and coplanar with the tray upper surface, and
wherein the channel outer wall has an outer wall radial distance, relative to the axis of symmetry, that is substantially equal to a maximum radial distance, relative to the axis of symmetry, of the opening of each of the adjacent wells of the plural wells in the sequence.

16. The system of claim 15, wherein each substantially circular opening has a respective center point located at a center point radial distance, relative to the axis of symmetry, and
wherein each channel inner wall has an inner wall radial distance, relative to the axis of symmetry, that is substantially equal to the center point radial distance, of each of the adjacent wells of the plural wells in the sequence.

17. The system of claim 12, further comprising a heater radially offset from the tray axis of symmetry and below the tray, wherein the heater and the wells are equally radially offset relative to the axis of symmetry.

* * * * *

UNITED STATES PATENT AND TRADEMARK OFFICE
CERTIFICATE OF CORRECTION

| | |
|---|---|
| PATENT NO. | : 11,446,652 B2 |
| APPLICATION NO. | : 17/595802 |
| DATED | : September 20, 2022 |
| INVENTOR(S) | : Jason Bryant et al. |

It is certified that error appears in the above-identified patent and that said Letters Patent is hereby corrected as shown below:

In the Claims

Column 8, Lines 6-7, in Claim 12, delete the wording "intersecting the openings of the adjacent ones of the plural wells in the respective sequence".

Signed and Sealed this
Fourteenth Day of February, 2023

Katherine Kelly Vidal
*Director of the United States Patent and Trademark Office*